United States Patent
Kaplan et al.

(10) Patent No.: US 11,566,136 B2
(45) Date of Patent: Jan. 31, 2023

(54) PH SENSITIVE DYES FOR TEXTILE MATERIALS, A PROCESS FOR THEIR PREPARATION AND USES THEREOF

(71) Applicant: Sanko Tekstil Isletmeleri San. Ve Tic. A.S., Inegol-Bursa (TR)

(72) Inventors: Gökhan Kaplan, Inegol-Bursa (TR); Gözde Öktem, Inegol-Bursa (TR); Deniz Iyidogan, Inegol-Bursa (TR); Olcay Bayar, Inegol-Bursa (TR); Semih Kazanc, Inegol-Bursa (TR); Özden Akman, Inegol-Bursa (TR)

(73) Assignee: Sanko Tekstil Isletmeleri San. Ve Tic. A.S., Inegol-Bursa (TR)

( * ) Notice: Subject to any disclaimer, the term of this patent is extended or adjusted under 35 U.S.C. 154(b) by 361 days.

(21) Appl. No.: 16/984,556

(22) Filed: Aug. 4, 2020

(65) Prior Publication Data
US 2021/0040325 A1   Feb. 11, 2021

(30) Foreign Application Priority Data

Aug. 5, 2019 (EP) .................................... 19190058

(51) Int. Cl.
*C09B 7/00* (2006.01)
*C09B 7/08* (2006.01)
*C07D 403/12* (2006.01)
*D06P 1/22* (2006.01)

(52) U.S. Cl.
CPC .............. *C09B 7/08* (2013.01); *C07D 403/12* (2013.01); *D06P 1/228* (2013.01)

(58) Field of Classification Search
CPC ......... C09B 7/08; C09B 57/00; C07D 403/12; C07D 209/40; D06P 1/228; D06P 1/227; D06P 1/00; G01N 31/221; G01N 21/78; C09K 9/02; C09K 2211/1029
USPC ............................................................ 8/653
See application file for complete search history.

(56) References Cited

U.S. PATENT DOCUMENTS

| | | | | |
|---|---|---|---|---|
| 3,793,341 A | * | 2/1974 | Genta ...................... | C09B 7/00 548/464 |
| 5,350,424 A | * | 9/1994 | Shansky ................ | A61K 8/411 8/408 |
| 5,350,425 A | * | 9/1994 | Carver .................... | C09B 7/00 8/651 |
| 2017/0362771 A1 | * | 12/2017 | Kaplan ................. | D06P 5/2005 |

FOREIGN PATENT DOCUMENTS

| EP | 3257900 | 12/2017 | | |
|---|---|---|---|---|
| EP | 3257900 B1 | * 11/2018 | ............... | C09B 7/04 |

OTHER PUBLICATIONS

STIC Search Report dated Sep. 20, 2022.*
European Search Report issued by the EPO dated Jan. 28, 2020 for EP priority application No. 19190058.8.

* cited by examiner

*Primary Examiner* — Eisa B Elhilo
(74) *Attorney, Agent, or Firm* — Silvia Salvadori

(57) ABSTRACT

The present invention relates to novel 3-oxindole derivatives, to a process for their preparation and to the use of said derivatives as dyes for manufacturing pH sensitive textiles and as indicators in titration methods. The invention also relates to a method to manufacture pH sensitive textiles and to textiles so obtained.

8 Claims, 5 Drawing Sheets

PH SENSITIVE DYES FOR TEXTILE MATERIALS, A PROCESS FOR THEIR PREPARATION AND USES THEREOF

This Non-Provisional Application claims priority to and the benefit of European Application No. EP19190058.8 filed on 5 Aug. 2019, the content of which is incorporated herein by reference in its entirety.

SUMMARY OF THE INVENTION

The present invention relates to novel 3-oxindole derivatives, to a process for their preparation and to the use of said derivatives as dyes for manufacturing pH sensitive textiles and as indicators in titration methods. The invention also relates to a method to manufacture pH sensitive textiles and to textiles so obtained.

TECHNICAL BACKGROUND

Color changeable dyes (chromic dyes) are known and used in many applications. These dyes can change upon an external stimulus, which can be light, heat, electric current, pressure, a solvent, pH or others.

There is an existing need for color changeable dyed textile materials, especially denim, i.e. materials colored with dyes that can be easily changed under conditions which can also be accessible to the final user, who can thus customize his own garments and textiles.

EP3257900 discloses dyes for textile materials showing irreversible color changeable properties, said dyes having an indigo structure.

Aims of the Invention

It is an aim of the invention to provide new compounds, which are useful, i.a., as dyes, especially as pH sensitive dyes or in titration methods.

It is a further aim of the invention to provide a process for the preparation of said new compounds.

It is a further aim of the invention to provide a method to manufacture textiles and in particular textiles that are pH sensitive.

It is a further aim of the invention to provide pH sensitive textiles and articles made therefrom.

These and further aims will be achieved by the subject-matter of the invention, as it will be herein below disclosed and claimed.

DESCRIPTION OF THE INVENTION

Figure 1:
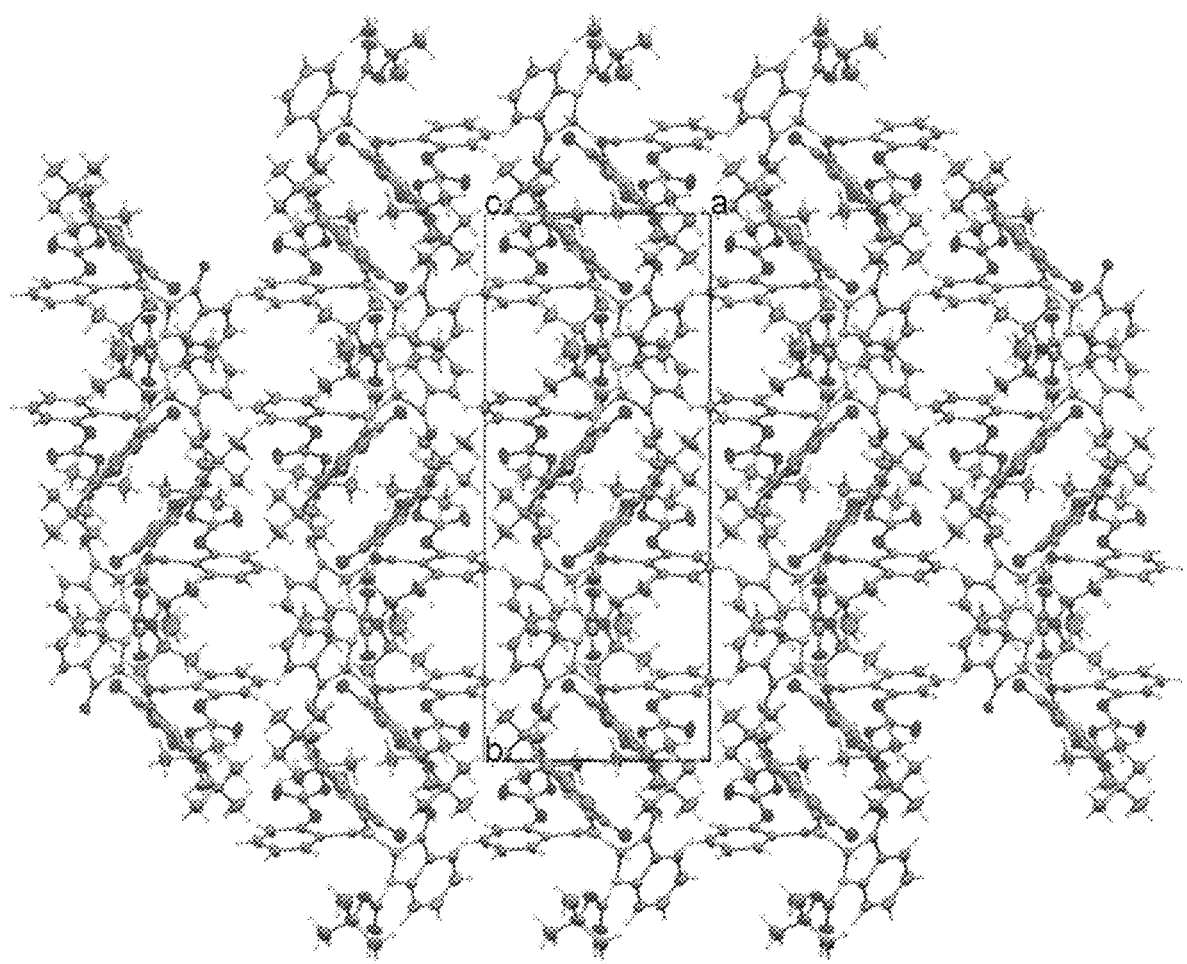
FIGS. 1 to 4 show the crystallographic data of a representative compound of the invention (Example 1).
Figure 2:
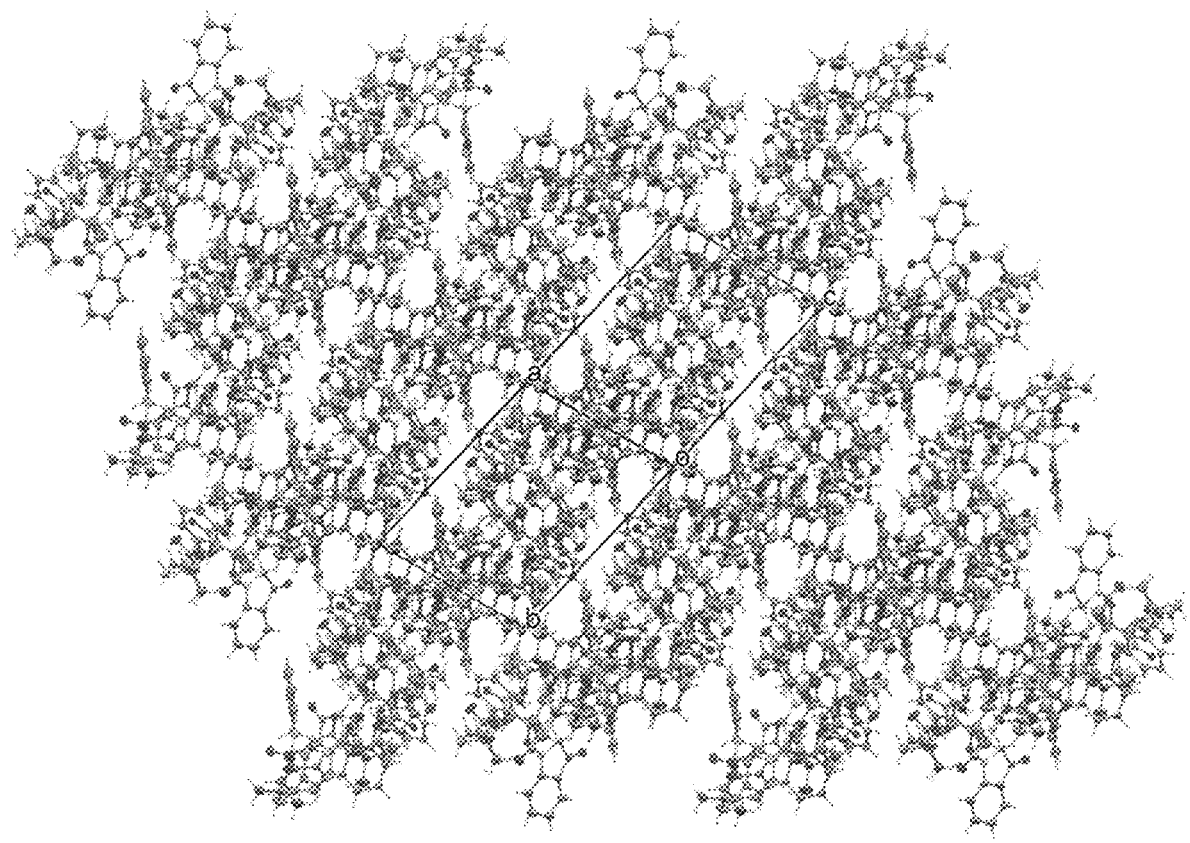
Figure 3:
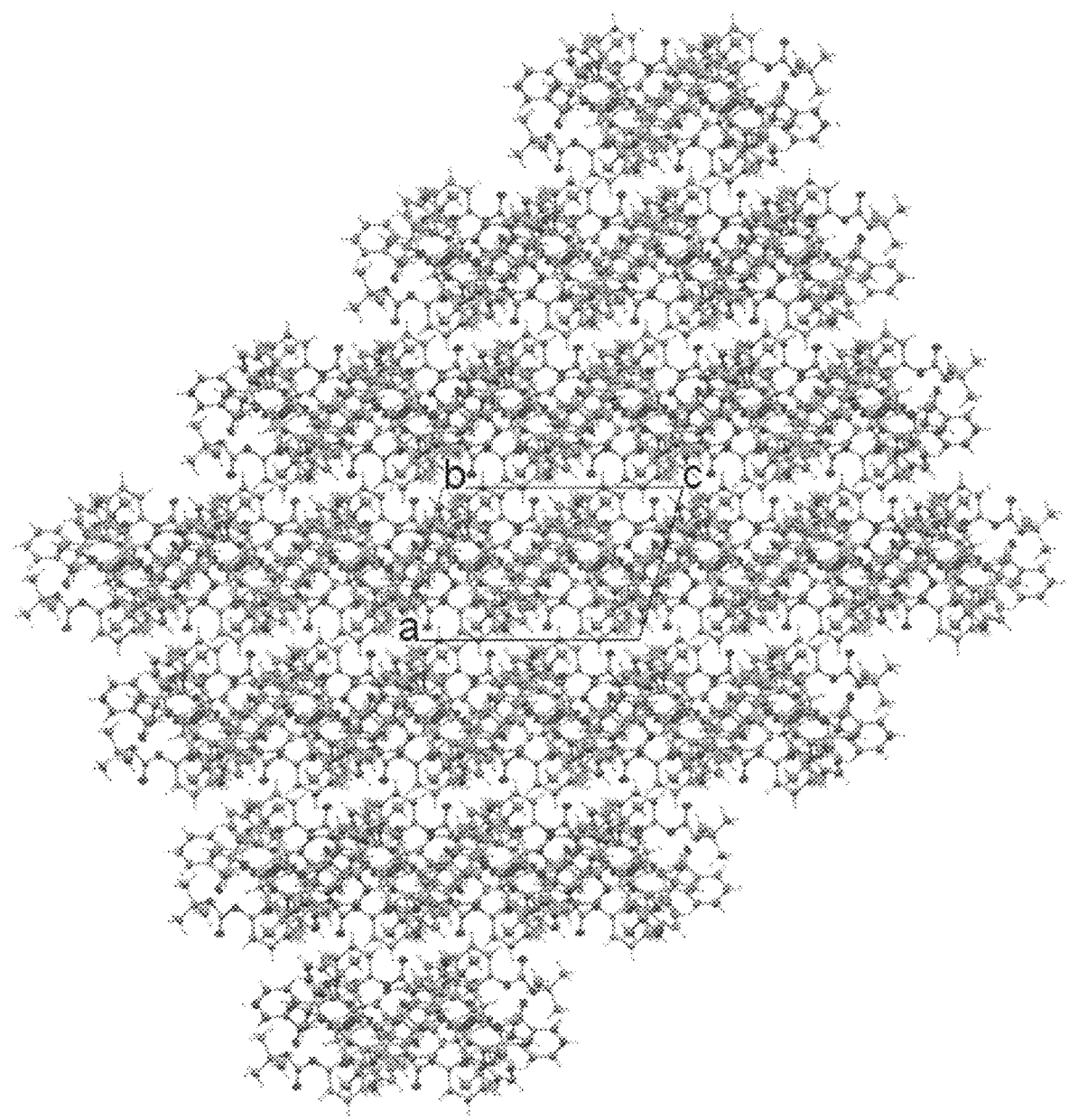
Figure 4:
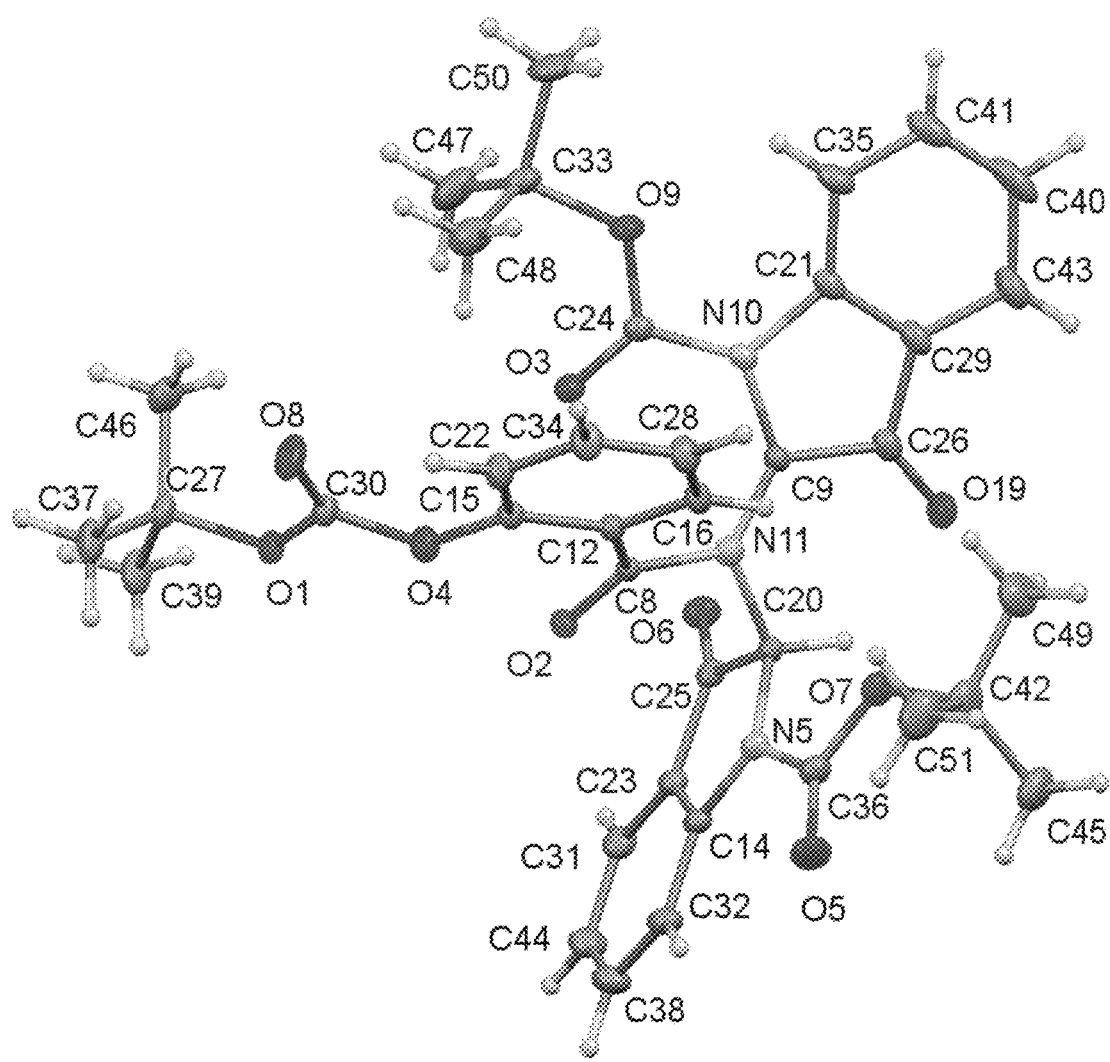

According to one of its aspects, the present invention relates to novel 3-oxindole compounds of formula (I)

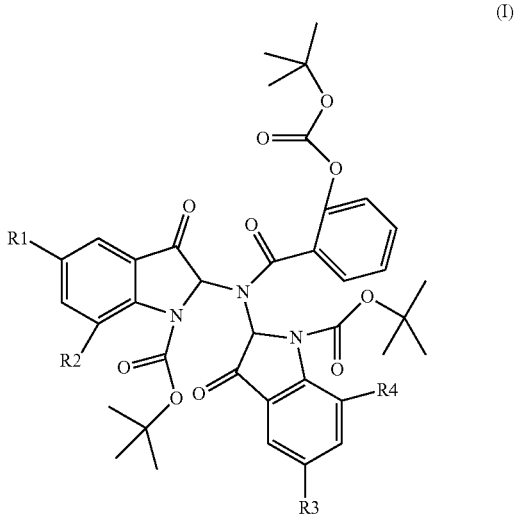

wherein $R_1$, $R_2$, $R_3$ and $R_4$ are, each independently, selected from a hydrogen atom, an alkyl group, an alkoxy group, a hydroxy group and a halogen atom, and salts and/or solvates thereof.

The expression "halogen atom" here indicates any one of the four halogen atoms, i.e. chlorine, bromine, iodine and fluorine, chlorine, bromine and iodine being preferred.

Alkyl groups are preferably selected from C1-C10, more preferably C1-C6 alkyl groups, such as methyl, ethyl, n-propyl, i-propyl, butyl groups, pentyl groups, hexyl groups, etc.

Alkoxy groups are preferably selected from C1-C10, more preferably C1-C6 alkoxy groups, such as methoxy, ethoxy, propoxy groups, butoxy groups etc.

According to a preferred embodiment, $R_1$, $R_2$, $R_3$ and $R_4$ are a hydrogen atom.

According to a preferred embodiment, compounds of formula (I) are not in the form of one of their salts and/or solvates.

The compounds of formula (I) may be synthesized by a reaction which comprises reacting t-Boc-protected indigo of formula (II)

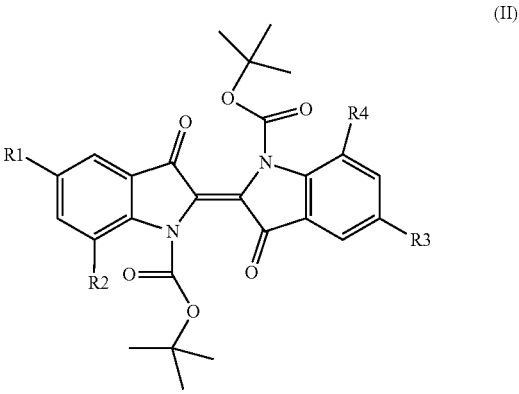

with sodium amide in a suitable organic solvent, adding an acid to obtain an acidic pH of the reaction mixture and isolating the compounds of formula (I).

The term "t-Boc" indicates the tert-butoxycarbonyl group.

According to a preferred embodiment, sodium amide is used in a molar excess with respect to the compound of formula (II), preferably the molar ratio compound of formula (II)/sodium amide is about 1/2 to 1/6, more preferably 1/3 to 1/5, most preferably about 1/4.

According to a preferred embodiment, the solvent used in the reaction is an alcohol, preferably selected from methanol, ethanol, n-propyl, i-propyl and butyl alcohols, more preferably i-propyl.

According to a preferred embodiment, the reaction is carried out at room temperature. The reaction is completed in a very short time and its development can be monitored by means of the conventional techniques such as Thin Layer Chromatography (TLC). In this case, any suitable solvent or solvent mixture can be used, for instance a mixture of ethyl acetate/hexane.

After completion, the reaction mixture is acidified by addition of a suitable acid, such as, for instance an aqueous solution of hydrochloric acid, and the compound of formula (I) is precipitated and can be isolated by conventional methods such as filtration. If desired, the filtrated compound can be purified, for example by crystallization, for instance from ethyl acetate. As it will be also disclosed below, the degree of purification of the product affects its color and the color of the textiles on which it is applied. Indeed, the crude product is usually red, whereas the color of the pure product is yellow.

If necessary or desired, the compound thus obtained can be converted in one of its salts according to the known methods.

Details of the process can be found in the Experimental Section of the present description.

The above process represents a further subject-matter of the invention.

According to another of its aspects, the invention relates to the use of compounds of formula (I) as dyes, especially as pH sensitive dyes and, in particular but not limited to, as pH sensitive dyes for textiles.

The compounds of the inventions may also be used as indicators in titration methods.

As used herein, terms "textile material(s)", "textile(s)" and "textile article(s)" are interchangeable and refer to any fibers, yarns, ropes, fabrics, textile articles and/or garments and/or household linen, able to be dyed. The textile materials may be of natural origin, such as the ones deriving from animals or plants, e.g. cotton, linen, silk, wool, etc., or may be of synthetic origin such as, polyesters, polyamides, regenerated cellulose, elastane, TPU, etc., or may be mixtures thereof, such as elasticized cotton fabrics or garments. Moreover, said yarns may be manufactured by any known method, and said fabrics also may be manufactured by any known method, such as weaving, knitting, crocheting, knotting, and felting. Furthermore, said garments may be any garment, such as jeans, shirts, casual wear garments, etc.

Preferably, the textile material is a fabric, more preferably a denim fabric.

Indeed, the novel compounds of formula (I) can be used as a dye in the textile industry, especially in the denim industry. The dye can be applied using many dyeing and/or printing techniques such as vat, pigment, Sulphur, solvent dyeing, and screen printing, digital printing, etc. An object of the invention is a textile comprising a compound of formula (1).

The color of the textile materials (such as fabric, yarn, rope, garment, curtain, etc.) dyed with novel pH-sensitive dye can be yellow, red or blue depending on the dyeing condition.

If the color of the dyed fabric is yellow/red and it turns blue after alkali washing (such as home washings with detergent or soap), this blue color will stay on the textile materials until it is washed with acidic solutions, e.g. by adding vinegar or lemon juice in the washing machine or in the washing tank, or by adding diluted acids, such as diluted citric acid, which do not damage the washing tank or machine.

The yellow/red color generally depends on the purification degree of the product.

Without any additional purification the color of the dyed textiles is red, however after purification of the compound the dyed textile color is yellow. The purification of the product may be carried out by any suitable technique, for example by crystallization from a suitable solvent, for instance from ethyl acetate or the like.

As an alternative, only part of the textile dyed with the compounds of formula (I), when it is yellow, can be washed/treated with basic solution such as soap, detergent or many diluted base solutions in order to have unique figures on the textile materials and these figures can be simply removed by acidic washings/treatments to obtain the original color of the textile materials back. In the same way, when the color of the dyed textile materials is blue, the color can be altered from blue to yellow or red upon acidic washings/treatments.

These color conversions may be repeated as many times as desired.

The above color conversion occurs when the pH is higher or lower than about 10. This interesting property of the compounds of formula (I) is due to the two acidic protons which are responsible for the color change, in the molecular structure. This molecular transformation provides for the color change. These acidic protons can be removed by adding a base in aqueous solution so that the indole rings are generated making the textile blue. By acidic treatment, the molecules turns back to the bis-3-oxindole compound and the color turns to yellow/red as shown in Scheme 1:

Scheme 1

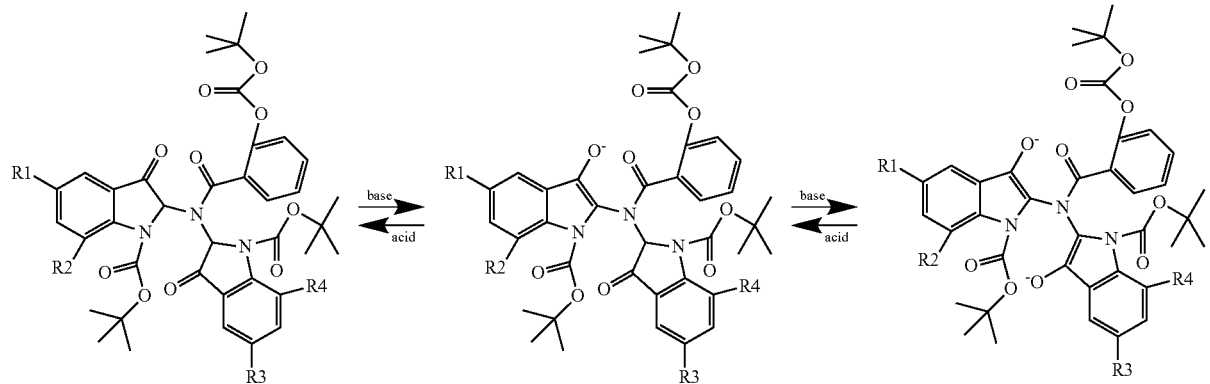

Compounds of formula (IIIA) and (IIIB)

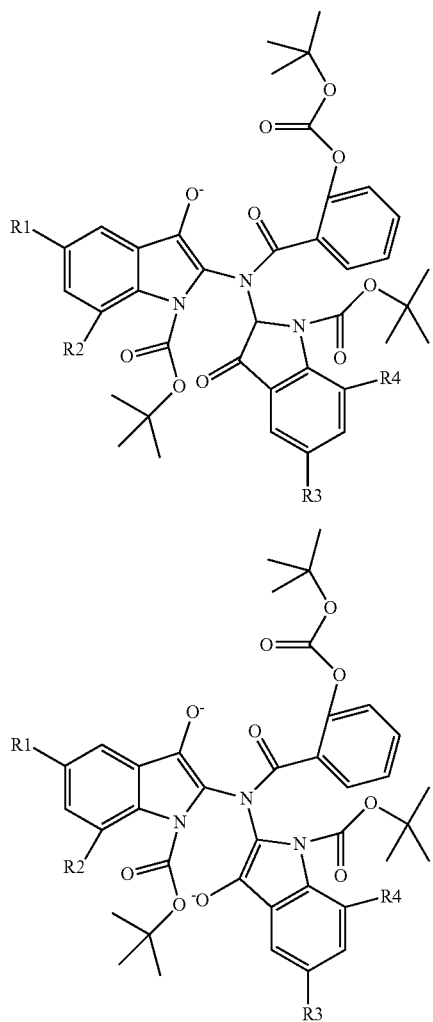

wherein $R_1$, $R_2$, $R_3$ and $R_4$ are as above defined, in the presence of a counter-ion, such as a metal counter-ion, for instance an alkali metal, for instance sodium, lithium or potassium, represent another aspect of the invention.

Applicant carried out tests on the UV absorption of different solutions comprising a representative compound of the invention, said solutions having a different pH.

Figure 5:
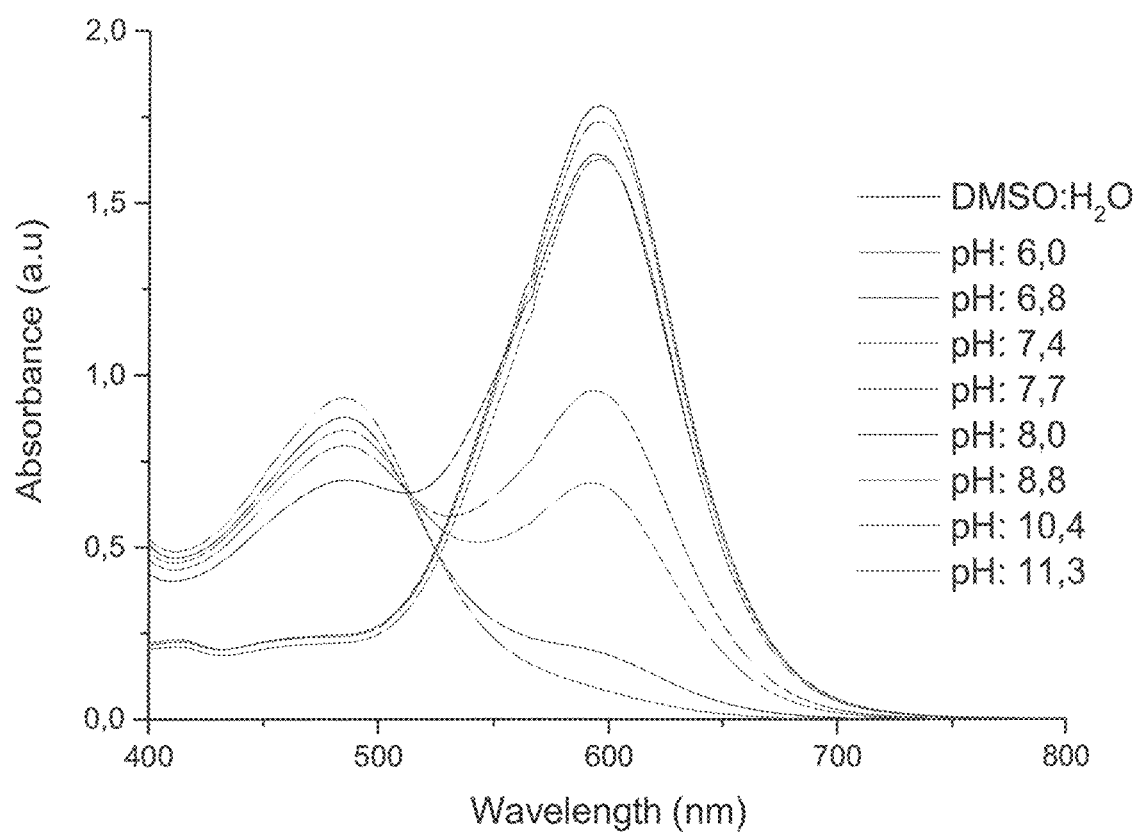
FIG. 5 shows UV-Vis absorptions of solutions containing a pH-sensitive compound of the invention at different pH.

As it can be seen in FIG. 5, changes in the pH of the solutions containing the pH-sensitive compound result in different UV absorptions, which shifts from yellow to blue by increasing the pH of said solutions.

The same effect can be directly seen on the above solutions and on textiles dyed with the pH-sensitive compounds of the invention, when washed with solutions having different pH.

According to another of its aspects, the invention relates to a method for pH sensitive dyeing textile materials, which comprises applying compounds of formula (I) onto a textile material.

Only one or a mixture of compounds of formula (I) may be used in the method of the invention. According to another of its aspects, the invention relates to a method for pH sensitive dyeing textile materials, which comprises applying compounds of formula (IIIA) or (IIIB) onto a textile material.

Only one or a mixture of compounds of formula (IIIA) or (IIIB) may be used in the method of the invention.

The dyeing solutions comprising the compounds of the invention can be prepared based on the pH according to the desired color of the textiles. Based on the present description, the skilled in the art is perfectly able to prepare said dyeing solutions.

The dyeing method can be performed according to the techniques known in the art.

For the dyeing method, generally one or more compounds of the invention are solubilized in a suitable aqueous solvent or solvent mixture, such as a water/alcohol mixture, wherein the alcohol is preferably selected from methanol, ethanol and isopropanol.

Generally, the impregnation step lasts 5-20 seconds, preferably about 10 seconds and is carried out preferably at room temperature.

Generally, drying time lasts a few minutes, such as 3-4 minutes, for instance about 2 minutes, preferably at 100-150° C., more preferably at about 120° C.

The textile material dyed according to the invention is another subject-matter of the invention and it may be used to produce articles, such as clothing garments such as, but not limited to, pants, skirts, shirts, hats and jackets but also household linen, etc.

As an alternative, articles, such as the above, may be dyed with the compounds of the invention according to the method of the invention.

An article obtained by the textile material dyed or directly dyed, according to the method of the invention is another subject-matter of the invention.

It can be easily understood that textiles dyed with the compounds of the invention allows for an unlimited number of possible applications, and that provides the final user with the possibility to customize his own textile articles, either by changing their whole color or by change only part of the color or also by creating patterns, figures and images on the textile articles, as well as to modify said colors, at will.

The invention will be disclosed in further detail in the following Experimental Section, in an illustrating and non-limiting way.

EXPERIMENTAL SECTION

Example 1

Preparation of a compound of formula (I) wherein $R_1$, $R_2$, $R_3$ and $R_4$ are all a hydrogen atom. 10 mmol (4.63 g) of t-Boc indigo (compound of formula (II) wherein $R_1$, $R_2$, $R_3$ and $R_4$ are all a hydrogen atom) is dissolved in 100 ml isopropyl alcohol at room temperature and stirred 15 min. before adding 40 mmol (160 mg) of sodium amide ($NaNH_2$). After adding sodium amide, the color of the reaction mixture turns from red-pink to dark blue in a few minutes. The reaction is monitored by Thin Layer Chromatography (TLC). The mixture ethyl acetate/hexane 1/3 is used as an eluent system for TLC. After completion of the reaction, the mixture is poured into the 1 M HCl solution to precipitate the product. The color of the mixture is altered with precipitation and solid part is collected after filtering by the sintered funnel. The collected solid part is crystallized from ethyl acetate and yellow crystals obtained in a good yield (65-75%). NMR Analysis:

$^1$H NMR (600 MHz, CDCl3) δ 9.92 (s, 1H), 8.43 (d, J=8.7 Hz, 1H), 7.94 (d, J=7.5 Hz, 1H), 7.87 (d, J=7.4 Hz, 1H), 7.73 (brd d, 1H), 7.65-7.56 (m, 3H), 7.49 (s, 1H), 7.47-7.41 (m, 1H), 7.29-7.20 (m, 14H), 6.85 (t, J=7.4 Hz, 1H), 1.47 (s, 9H), 1.42 (s, 9H), 1.32 (s, 9H).

Elemental Analysis:

$C_{38}H_{41}N_3O_{10}$ (Molecular Weight: 699, 75 g/mol),

Found: C (65.22%), H (5.91%), N (6.01%), O (22.86%).

Calculated: C (66.42%), H (6.17%), N (5.46%), O (21.95%).

Crystal Analysis:

Crystal data of the product is provided in FIGS. 1 to 4 and in the following Tables 1 to 5.

TABLE 1

Fractional atomic coordinates and isotropic temperature factors (Angstrom squared), with standard deviations in the least significant digits in parentheses. For anisotropic atoms, the equivalent isotropic temperature factors are shown.

| | x/a | y/b | z/c | U |
|---|---|---|---|---|
| O(1) | 0.2980(2) | 0.0515(1) | 0.4779(1) | 0.05991 |
| O(2) | 0.4795(2) | 0.1287(1) | 0.3301(1) | 0.05548 |
| O(3) | 0.3726(2) | 0.0302(1) | 0.2249(2) | 0.06090 |
| O(4) | 0.2554(3) | 0.1004(1) | 0.3616(2) | 0.07436 |
| N(5) | 0.5885(3) | 0.2196(1) | 0.2571(2) | 0.05507 |
| O(6) | 0.7636(2) | 0.0954(1) | 0.2767(2) | 0.07054 |
| O(9) | 0.2465(3) | −0.0110(1) | 0.1070(2) | 0.07667 |
| C(8) | 0.4150(3) | 0.1314(1) | 0.2549(2) | 0.04408 |

TABLE 1-continued

Fractional atomic coordinates and isotropic temperature factors (Angstrom squared), with standard deviations in the least significant digits in parentheses. For anisotropic atoms, the equivalent isotropic temperature factors are shown.

| | x/a | y/b | z/c | U |
|---|---|---|---|---|
| C(9) | 0.4703(3) | 0.1003(1) | 0.1199(2) | 0.04759 |
| N(10) | 0.3712(3) | 0.0597(1) | 0.0913(2) | 0.05335 |
| N(11) | 0.4911(3) | 0.1318(1) | 0.1896(2) | 0.06109 |
| C(12) | 0.2717(3) | 0.1377(1) | 0.2273(2) | 0.04713 |
| O(7) | 0.4731(3) | 0.2483(1) | 0.1299(2) | 0.07777 |
| C(14) | 0.6781(3) | 0.2239(1) | 0.3388(2) | 0.05680 |
| C(15) | 0.1930(3) | 0.1218(1) | 0.2806(2) | 0.05024 |
| C(16) | 0.2112(3) | 0.1584(1) | 0.1460(2) | 0.05556 |
| H(16) | 0.26213 | 0.16954 | 0.11104 | 0.06668 |
| O(5) | 0.5157(3) | 0.3074(1) | 0.2426(2) | 0.09171 |
| O(8) | 0.0873(3) | 0.0567(2) | 0.3972(2) | 0.09495 |
| O(19) | 0.6275(3) | 0.1362(1) | 0.0481(2) | 0.07968 |
| C(20) | 0.6100(3) | 0.1680(1) | 0.2156(2) | 0.04960 |
| H(20) | 0.64049 | 0.17621 | 0.16552 | 0.05952 |
| C(21) | 0.3590(3) | 0.0477(2) | 0.0026(2) | 0.05932 |
| C(22) | 0.0576(3) | 0.1264(2) | 0.2500(3) | 0.06454 |
| H(22) | 0.00519 | 0.11615 | 0.28449 | 0.07744 |
| C(23) | 0.7584(3) | 0.1784(1) | 0.3560(2) | 0.05859 |
| C(24) | 0.3324(3) | 0.0258(1) | 0.1481(2) | 0.05434 |
| C(25) | 0.7212(3) | 0.1397(1) | 0.2850(2) | 0.05472 |
| C(26) | 0.5310(4) | 0.1090(2) | 0.0472(2) | 0.06287 |
| C(27) | 0.2756(4) | 0.0090(2) | 0.5371(2) | 0.06431 |
| C(28) | 0.0755(4) | 0.1627(2) | 0.1166(3) | 0.06884 |
| H(28) | 0.03579 | 0.17658 | 0.06246 | 0.08261 |
| C(29) | 0.4499(4) | 0.0782(2) | −0.0240(2) | 0.06628 |
| C(30) | 0.2013(3) | 0.0681(2) | 0.4108(2) | 0.05807 |
| C(31) | 0.8594(4) | 0.1735(2) | 0.4323(2) | 0.07489 |
| H(31) | 0.91553 | 0.14361 | 0.44240 | 0.08986 |
| C(32) | 0.6913(4) | 0.2649(2) | 0.3993(3) | 0.07434 |
| H(32) | 0.63612 | 0.29511 | 0.38937 | 0.08921 |
| C(33) | 0.1763(4) | −0.0478(2) | 0.1521(3) | 0.07774 |
| C(34) | 0.0013(4) | 0.1461(2) | 0.1689(3) | 0.07321 |
| H(34) | −0.08929 | 0.14832 | 0.14899 | 0.08785 |
| C(35) | 0.2739(4) | 0.0130(2) | −0.0536(3) | 0.07733 |
| H(35) | 0.21236 | −0.00732 | −0.03589 | 0.09280 |
| C(36) | 0.5234(4) | 0.2633(2) | 0.2119(3) | 0.06723 |
| C(37) | 0.1789(5) | 0.0275(2) | 0.5823(3) | 0.09006 |
| H(37A) | 0.21033 | 0.06012 | 0.61409 | 0.13509 |
| H(37B) | 0.16742 | −0.00060 | 0.62062 | 0.13509 |
| H(37C) | 0.09673 | 0.03492 | 0.54111 | 0.13509 |
| C(38) | 0.7890(5) | 0.2594(2) | 0.4744(3) | 0.09221 |
| H(38) | 0.79971 | 0.28684 | 0.51533 | 0.11065 |
| C(39) | 0.4094(4) | 0.0038(2) | 0.6004(3) | 0.09126 |
| H(39A) | 0.47209 | −0.00638 | 0.57077 | 0.13689 |
| H(39B) | 0.40689 | −0.02365 | 0.64201 | 0.13689 |
| H(39C) | 0.43410 | 0.03818 | 0.62871 | 0.13689 |
| C(40) | 0.3713(7) | 0.0389(3) | −0.1626(3) | 0.11908 |
| H(40) | 0.37447 | 0.03510 | −0.21880 | 0.14290 |
| C(41) | 0.2824(5) | 0.0093(3) | −0.1356(3) | 0.09559 |
| H(41) | 0.22625 | −0.01410 | −0.17375 | 0.11471 |
| C(42) | 0.4160(5) | 0.2904(2) | 0.0633(3) | 0.09117 |
| C(43) | 0.4592(5) | 0.0755(2) | −0.1080(3) | 0.09115 |
| H(43) | 0.51905 | 0.09624 | −0.12657 | 0.10938 |
| C(44) | 0.8719(5) | 0.2149(2) | 0.4918(3) | 0.09037 |
| H(44) | 0.93630 | 0.21278 | 0.54368 | 0.10845 |
| O(45) | 0.5168(6) | 0.3334(2) | 0.0626(4) | 0.11213 |
| H(45A) | 0.52348 | 0.35819 | 0.10925 | 0.16820 |
| H(45B) | 0.49121 | 0.35307 | 0.00961 | 0.16820 |
| H(45C) | 0.59985 | 0.31621 | 0.06858 | 0.16820 |
| C(46) | 0.2344(7) | −0.0426(2) | 0.4877(4) | 0.10812 |
| H(46A) | 0.14962 | −0.03761 | 0.44823 | 0.16218 |
| H(46B) | 0.23103 | −0.07174 | 0.52642 | 0.16218 |
| H(46C) | 0.29630 | −0.05152 | 0.45672 | 0.16218 |
| C(47) | 0.2691(5) | −0.0827(2) | 0.2179(4) | 0.11301 |
| H(47A) | 0.32543 | −0.10233 | 0.19150 | 0.16951 |
| H(47B) | 0.22017 | −0.10815 | 0.24168 | 0.16951 |
| H(47C) | 0.32069 | −0.05987 | 0.26262 | 0.16951 |
| C(48) | 0.0925(5) | −0.0134(2) | 0.1933(4) | 0.10373 |
| H(48A) | 0.14740 | 0.01000 | 0.23566 | 0.15559 |
| H(48B) | 0.04312 | −0.03685 | 0.21997 | 0.15559 |
| H(48C) | 0.03372 | 0.00844 | 0.15048 | 0.15559 |
| C(49) | 0.3834(7) | 0.2559(3) | −0.0166(3) | 0.12510 |
| H(49A) | 0.31859 | 0.22933 | −0.01368 | 0.18764 |

TABLE 1-continued

Fractional atomic coordinates and isotropic temperature factors (Angstrom squared), with standard deviations in the least significant digits in parentheses. For anisotropic atoms, the equivalent isotropic temperature factors are shown.

| | x/a | y/b | z/c | U |
|---|---|---|---|---|
| H(49B) | 0.46083 | 0.23761 | −0.02125 | 0.18764 |
| H(49C) | 0.35017 | 0.27885 | −0.06562 | 0.18764 |
| C(50) | 0.0916(7) | −0.0807(3) | 0.0777(4) | 0.13939 |
| H(50A) | 0.03400 | −0.05649 | 0.03823 | 0.20908 |
| H(50B) | 0.04108 | −0.10679 | 0.09890 | 0.20908 |
| H(50C) | 0.14649 | −0.09948 | 0.04914 | 0.20908 |
| C(51) | 0.2926(6) | 0.3138(3) | 0.0793(5) | 0.12436 |
| H(51A) | 0.23166 | 0.28484 | 0.07862 | 0.18655 |
| H(51B) | 0.25399 | 0.33982 | 0.03538 | 0.18655 |
| H(51C) | 0.31432 | 0.33162 | 0.13397 | 0.18655 |

TABLE 2

Vibration parameters (Angstrom squared) in the expression:
$-2(\pi^2)(U_{11}(h.a^*)^2 + U_{22}(k.b^*)^2 + U_{33}(l.c^*)^2 + 2.U_{12}.h.k.a^*.b^* + 2.U_{13}.h.l.a^*.c^* + 2.U_{23}.k.l.b^*.c^*)$

| | U11 | U22 | U33 | U12 | U13 | U23 |
|---|---|---|---|---|---|---|
| O(1) | 0.055(1) | 0.071(2) | 0.052(1) | −0.005(1) | 0.011(1) | 0.015(1) |
| O(2) | 0.054(1) | 0.068(1) | 0.043(1) | −0.009(1) | 0.010(1) | −0.001(1) |
| O(3) | 0.063(1) | 0.055(1) | 0.059(2) | −0.006(1) | 0.007(1) | 0.003(1) |
| O(4) | 0.072(2) | 0.085(2) | 0.066(2) | −0.002(1) | 0.019(1) | 0.010(1) |
| N(5) | 0.062(2) | 0.041(1) | 0.062(2) | −0.002(1) | 0.018(1) | 0.001(1) |
| O(6) | 0.058(1) | 0.059(2) | 0.092(2) | 0.009(1) | 0.015(1) | −0.004(1) |
| O(9) | 0.083(2) | 0.067(2) | 0.073(2) | −0.026(1) | 0.012(1) | −0.015(1) |
| C(8) | 0.050(2) | 0.039(1) | 0.044(2) | −0.004(1) | 0.015(1) | −0.001(1) |
| C(9) | 0.053(2) | 0.045(2) | 0.044(2) | 0.003(1) | 0.012(1) | −0.001(1) |
| N(10) | 0.057(2) | 0.053(2) | 0.046(1) | 0.003(1) | 0.008(1) | −0.008(1) |
| N(11) | 0.066(2) | 0.056(2) | 0.060(2) | 0.003(1) | 0.014(1) | 0.005(1) |
| C(12) | 0.050(2) | 0.046(2) | 0.046(2) | 0.003(1) | 0.015(1) | 0.001(1) |
| O(7) | 0.097(2) | 0.052(1) | 0.075(2) | 0.007(1) | 0.010(2) | 0.017(1) |
| C(14) | 0.063(2) | 0.047(2) | 0.059(2) | −0.013(2) | 0.015(2) | −0.002(1) |
| C(15) | 0.051(2) | 0.050(2) | 0.048(2) | 0.004(1) | 0.010(1) | 0.003(1) |
| C(16) | 0.059(2) | 0.057(2) | 0.049(2) | 0.009(2) | 0.013(1) | 0.009(1) |
| O(5) | 0.120(2) | 0.047(2) | 0.104(2) | 0.013(2) | 0.025(2) | −0.004(2) |
| O(8) | 0.052(2) | 0.131(3) | 0.094(2) | −0.017(2) | 0.008(1) | 0.047(2) |
| O(19) | 0.084(2) | 0.091(2) | 0.076(2) | −0.010(2) | 0.042(2) | −0.003(2) |
| C(20) | 0.053(2) | 0.044(2) | 0.053(2) | −0.003(1) | 0.017(1) | 0.001(1) |
| C(21) | 0.061(2) | 0.063(2) | 0.048(2) | 0.018(2) | 0.005(2) | −0.008(2) |
| C(22) | 0.053(2) | 0.077(2) | 0.066(2) | 0.011(2) | 0.022(2) | 0.014(2) |
| C(23) | 0.058(2) | 0.054(2) | 0.060(2) | −0.014(2) | 0.012(2) | −0.003(2) |
| C(24) | 0.053(2) | 0.045(2) | 0.061(2) | 0.003(1) | 0.009(2) | −0.005(2) |
| C(25) | 0.046(2) | 0.052(2) | 0.067(2) | −0.006(1) | 0.017(2) | 0.002(2) |
| C(26) | 0.072(2) | 0.065(2) | 0.053(2) | 0.013(2) | 0.020(2) | −0.002(2) |
| C(27) | 0.067(2) | 0.066(2) | 0.061(2) | −0.004(2) | 0.019(2) | 0.021(2) |
| C(28) | 0.063(2) | 0.079(3) | 0.058(2) | 0.019(2) | 0.006(2) | 0.017(2) |
| C(29) | 0.068(2) | 0.082(3) | 0.049(2) | 0.019(2) | 0.016(2) | −0.005(2) |
| C(30) | 0.056(2) | 0.064(2) | 0.055(2) | −0.003(2) | 0.016(2) | 0.011(2) |
| C(31) | 0.060(2) | 0.080(3) | 0.075(2) | −0.015(2) | 0.004(2) | 0.008(2) |
| C(32) | 0.078(3) | 0.061(2) | 0.083(3) | −0.015(2) | 0.021(2) | −0.018(2) |
| C(33) | 0.074(3) | 0.056(2) | 0.100(3) | −0.016(2) | 0.018(2) | −0.011(2) |
| C(34) | 0.048(2) | 0.091(3) | 0.077(3) | 0.016(2) | 0.011(2) | 0.017(2) |
| C(35) | 0.078(3) | 0.086(3) | 0.059(2) | 0.007(2) | 0.003(2) | −0.022(2) |
| C(36) | 0.078(2) | 0.051(2) | 0.071(2) | −0.002(2) | 0.018(2) | 0.003(2) |
| C(37) | 0.079(3) | 0.121(4) | 0.079(3) | 0.002(3) | 0.037(2) | 0.029(3) |
| C(38) | 0.102(3) | 0.089(3) | 0.079(3) | −0.027(3) | 0.014(3) | −0.029(3) |
| C(39) | 0.072(3) | 0.124(4) | 0.075(3) | 0.012(3) | 0.016(2) | 0.040(3) |
| C(40) | 0.111(4) | 0.176(6) | 0.058(3) | 0.060(4) | 0.005(3) | −0.038(3) |
| C(41) | 0.086(3) | 0.120(4) | 0.070(3) | 0.020(3) | 0.003(3) | −0.034(3) |
| C(42) | 0.107(3) | 0.075(3) | 0.083(3) | 0.021(3) | 0.011(3) | 0.032(2) |
| C(43) | 0.090(3) | 0.126(4) | 0.060(2) | 0.022(3) | 0.024(2) | −0.006(3) |
| C(44) | 0.085(3) | 0.094(3) | 0.076(3) | −0.024(3) | −0.002(2) | −0.013(3) |
| C(45) | 0.119(4) | 0.091(4) | 0.118(4) | −0.008(3) | 0.020(3) | 0.047(3) |
| C(46) | 0.148(5) | 0.075(3) | 0.102(4) | −0.023(3) | 0.038(3) | 0.010(3) |
| C(47) | 0.095(3) | 0.075(3) | 0.171(6) | −0.004(3) | 0.040(4) | 0.027(3) |
| C(48) | 0.084(3) | 0.087(3) | 0.145(5) | −0.005(3) | 0.038(3) | −0.009(3) |

TABLE 2-continued

Vibration parameters (Angstrom squared) in the expression:
$-2(\pi^2)(U_{11}(h.a^*)^2 + U_{22}(k.b^*)^2 + U_{33}(l.c^*)^2 + 2.U_{12}.h.k.a^*.b^* + 2.U_{13}.h.l.a^*.c^* + 2.U_{23}.k.l.b^*.c^*)$

| | U11 | U22 | U33 | U12 | U13 | U23 |
|---|---|---|---|---|---|---|
| C(49) | 0.154(5) | 0.121(5) | 0.077(3) | 0.003(4) | −0.007(3) | 0.029(3) |
| C(50) | 0.155(6) | 0.113(5) | 0.141(5) | −0.081(4) | 0.027(4) | −0.042(4) |
| C(51) | 0.103(4) | 0.106(4) | 0.155(6) | 0.025(3) | 0.020(4) | 0.050(4) |

TABLE 3

Complete listing of bond distances (Angstroms)

| | | | |
|---|---|---|---|
| O(1)—C(30) | 1.340(5) | O(2)—C(8) | 1.227(4) |
| O(3)—C(24) | 1.208(5) | O(4)—C(15) | 1.403(5) |
| O(4)—C(30) | 1.363(5) | N(5)—C(14) | 1.410(5) |
| N(5)—C(36) | 1.373(5) | O(6)—C(25) | 1.196(5) |
| O(9)—C(24) | 1.326(5) | C(8)—C(12) | 1.475(5) |
| C(9)—N(10) | 1.431(5) | C(9)—N(11) | 1.340(5) |
| C(9)—C(26) | 1.512(5) | N(10)—C(21) | 1.444(5) |
| N(10)—C(24) | 1.388(5) | C(12)—C(15) | 1.418(5) |
| C(12)—C(16) | 1.397(5) | O(7)—C(36) | 1.343(6) |
| C(14)—C(23) | 1.384(5) | C(14)—C(32) | 1.387(6) |
| C(15)—C(22) | 1.393(5) | C(16)—H(16) | 0.930(4) |
| C(16)—C(28) | 1.395(6) | O(5)—C(36) | 1.204(5) |
| O(8)—C(30) | 1.205(5) | O(19)—C(26) | 1.223(6) |
| C(20)—H(20) | 0.980(4) | C(21)—C(29) | 1.386(6) |
| C(21)—C(35) | 1.386(6) | C(22)—H(22) | 0.930(4) |
| C(22)—C(34) | 1.378(6) | C(23)—C(25) | 1.463(5) |
| C(23)—C(31) | 1.404(6) | C(26)—C(29) | 1.450(6) |
| C(27)—C(37) | 1.494(7) | C(27)—C(39) | 1.515(6) |
| C(27)—C(46) | 1.496(7) | C(28)—H(28) | 0.930(4) |
| C(28)—C(34) | 1.375(6) | C(29)—C(43) | 1.400(6) |
| C(31)—H(31) | 0.930(5) | C(31)—C(44) | 1.384(7) |
| C(32)—H(32) | 0.930(5) | C(32)—C(38) | 1.375(7) |
| C(33)—C(47) | 1.506(8) | C(33)—C(48) | 1.514(8) |
| C(33)—C(50) | 1.524(8) | C(34)—H(34) | 0.930(4) |
| C(35)—H(35) | 0.930(5) | C(35)—C(41) | 1.367(7) |
| C(37)—H(37A) | 0.960(6) | C(37)—H(37B) | 0.960(6) |
| C(37)—H(37C) | 0.960(5) | C(38)—H(38) | 0.930(6) |
| C(38)—C(44) | 1.382(8) | C(39)—H(39A) | 0.960(5) |
| C(39)—H(39B) | 0.960(6) | C(39)—H(39C) | 0.960(6) |
| C(40)—H(40) | 0.930(6) | C(40)—C(41) | 1.361(9) |
| C(40)—C(43) | 1.416(9) | C(41)—H(41) | 0.930(6) |
| C(42)—C(45) | 1.505(8) | C(42)—C(49) | 1.508(8) |
| C(42)—C(51) | 1.523(9) | C(43)—H(43) | 0.930(6) |
| C(44)—H(44) | 0.930(5) | C(45)—H(45A) | 0.960(6) |
| C(45)—H(45B) | 0.960(6) | C(45)—H(45C) | 0.960(6) |
| C(46)—H(46A) | 0.960(7) | C(46)—H(46B) | 0.960(6) |
| C(46)—H(46C) | 0.960(7) | C(47)—H(47A) | 0.960(6) |
| C(47)—H(47B) | 0.960(6) | C(47)—H(47C) | 0.960(7) |
| C(48)—H(48A) | 0.960(6) | C(48)—H(48B) | 0.960(6) |
| C(48)—H(48C) | 0.960(6) | C(49)—H(49A) | 0.960(7) |
| C(49)—H(49B) | 0.960(8) | C(49)—H(49C) | 0.960(6) |
| C(50)—H(50A) | 0.960(7) | C(50)—H(50B) | 0.960(7) |
| C(50)—H(50C) | 0.960(8) | C(51)—H(51A) | 0.960(7) |
| C(51)—H(51B) | 0.960(7) | C(51)—H(51C) | 0.960(7) |

TABLE 4

Complete listing of bond angles (degrees)

| | | | |
|---|---|---|---|
| C(15)—O(4)—C(30) | 127.0(3) | C(14)—N(5)—C(36) | 123.9(3) |
| O(2)—C(8)—C(12) | 123.6(3) | N(10)—C(9)—N(11) | 127.5(3) |
| N(10)—C(9)—C(26) | 106.3(3) | N(11)—C(9)—C(26) | 125.2(3) |
| C(9)—N(10)—C(21) | 108.6(3) | C(9)—N(10)—C(24) | 121.9(3) |
| C(21)—N(10)—C(24) | 125.8(3) | C(8)—C(12)—C(15) | 121.6(3) |
| C(8)—C(12)—C(16) | 119.5(3) | C(15)—C(12)—C(16) | 119.0(3) |
| N(5)—C(14)—C(23) | 110.4(3) | N(5)—C(14)—C(32) | 129.3(4) |
| C(23)—C(14)—C(32) | 120.3(4) | O(4)—C(15)—C(12) | 118.1(3) |
| O(4)—C(15)—C(22) | 122.6(3) | C(12)—C(15)—C(22) | 119.3(3) |
| C(12)—C(16)—H(16) | 119.6(4) | C(12)—C(16)—C(28) | 120.8(4) |
| H(16)—C(16)—C(28) | 119.6(4) | N(10)—C(21)—C(29) | 109.1(3) |

TABLE 4-continued

Complete listing of bond angles (degrees)

| Atoms | Angle | Atoms | Angle |
|---|---|---|---|
| N(10)—C(21)—C(35) | 130.2(4) | C(29)—C(21)—C(35) | 120.6(4) |
| C(15)—C(22)—H(22) | 119.9(4) | C(15)—C(22)—C(34) | 120.1(4) |
| H(22)—C(22)—C(34) | 119.9(4) | C(14)—C(23)—C(25) | 110.2(4) |
| C(14)—C(23)—C(31) | 121.7(4) | C(25)—C(23)—C(31) | 128.0(4) |
| O(3)—C(24)—O(9) | 125.4(4) | O(3)—C(24)—N(10) | 123.4(4) |
| O(9)—C(24)—N(10) | 111.2(3) | O(6)—C(25)—C(23) | 130.5(4) |
| C(9)—C(26)—O(19) | 127.5(4) | C(9)—C(26)—C(29) | 105.3(4) |
| O(19)—C(26)—C(29) | 127.2(4) | C(37)—C(27)—C(39) | 109.7(4) |
| C(37)—C(27)—C(46) | 112.4(5) | C(39)—C(27)—C(46) | 112.0(5) |
| C(16)—C(28)—H(28) | 120.5(4) | C(16)—C(28)—C(34) | 119.1(4) |
| H(28)—C(28)—C(34) | 120.5(4) | C(21)—C(29)—C(26) | 110.0(4) |
| C(21)—C(29)—C(43) | 121.7(4) | C(26)—C(29)—C(43) | 128.2(4) |
| O(1)—C(30)—O(4) | 107.5(3) | O(1)—C(30)—O(8) | 125.9(4) |
| O(4)—C(30)—O(8) | 126.6(4) | C(23)—C(31)—H(31) | 121.4(5) |
| C(23)—C(31)—C(44) | 117.2(4) | H(31)—C(31)—C(44) | 121.4(5) |
| C(14)—C(32)—H(32) | 121.2(5) | C(14)—C(32)—C(38) | 117.6(4) |
| H(32)—C(32)—C(38) | 121.2(5) | C(47)—C(33)—C(48) | 110.6(5) |
| C(47)—C(33)—C(50) | 113.1(5) | C(48)—C(33)—C(50) | 110.8(5) |
| C(22)—C(34)—C(28) | 121.7(4) | C(22)—C(34)—H(34) | 119.2(4) |
| C(28)—C(34)—H(34) | 119.2(5) | C(21)—C(35)—H(35) | 120.8(4) |
| C(21)—C(35)—C(41) | 118.5(5) | H(35)—C(35)—C(41) | 120.7(5) |
| N(5)—C(36)—O(7) | 108.9(4) | N(5)—C(36)—O(5) | 124.0(4) |
| O(7)—C(36)—O(5) | 127.1(4) | C(27)—C(37)—H(37A) | 109.5(5) |
| C(27)—C(37)—H(37B) | 109.5(5) | C(27)—C(37)—H(37C) | 109.5(5) |
| H(37A)—C(37)—H(37B) | 109.5(5) | H(37A)—C(37)—H(37C) | 109.5(6) |
| H(37B)—C(37)—H(37C) | 109.5(5) | C(32)—C(38)—H(38) | 118.6(6) |
| C(32)—C(38)—C(44) | 122.8(5) | H(38)—C(38)—C(44) | 118.6(5) |
| C(27)—C(39)—H(39A) | 109.5(4) | C(27)—C(39)—H(39B) | 109.5(5) |
| C(27)—C(39)—H(39C) | 109.5(5) | H(39A)—C(39)—H(39B) | 109.5(6) |
| H(39A)—C(39)—H(39C) | 109.5(5) | H(39B)—C(39)—H(39C) | 109.5(5) |
| H(40)—C(40)—C(41) | 118.9(7) | H(40)—C(40)—C(43) | 118.9(7) |
| C(41)—C(40)—C(43) | 122.1(5) | C(35)—C(41)—C(40) | 121.5(6) |
| C(35)—C(41)—H(41) | 119.3(6) | C(40)—C(41)—H(41) | 119.3(6) |
| C(45)—C(42)—C(49) | 112.3(5) | C(45)—C(42)—C(51) | 112.9(5) |
| C(49)—C(42)—C(51) | 110.9(5) | C(29)—C(43)—C(40) | 115.5(5) |
| C(29)—C(43)—H(43) | 122.3(5) | C(40)—C(43)—H(43) | 122.3(5) |
| C(31)—C(44)—C(38) | 120.2(5) | C(31)—C(44)—H(44) | 119.9(6) |
| C(38)—C(44)—H(44) | 119.9(6) | C(42)—C(45)—H(45A) | 109.5(6) |
| C(42)—C(45)—H(45B) | 109.5(6) | C(42)—C(45)—H(45C) | 109.5(6) |
| H(45A)—C(45)—H(45B) | 109.5(6) | H(45A)—C(45)—H(45C) | 109.5(6) |
| H(45B)—C(45)—H(45C) | 109.5(6) | C(27)—C(46)—H(46A) | 109.5(5) |
| C(27)—C(46)—H(46B) | 109.5(5) | C(27)—C(46)—H(46C) | 109.5(6) |
| H(46A)—C(46)—H(46B) | 109.5(7) | H(46A)—C(46)—H(46C) | 109.5(6) |
| H(46B)—C(46)—H(46C) | 109.5(6) | C(33)—C(47)—H(47A) | 109.5(6) |
| C(33)—C(47)—H(47B) | 109.5(5) | C(33)—C(47)—H(47C) | 109.5(5) |
| H(47A)—C(47)—H(47B) | 109.5(6) | H(47A)—C(47)—H(47C) | 109.5(6) |
| H(47B)—C(47)—H(47C) | 109.5(7) | C(33)—C(48)—H(48A) | 109.5(5) |
| C(33)—C(48)—H(48B) | 109.5(5) | C(33)—C(48)—H(48C) | 109.5(6) |
| H(48A)—C(48)—H(48B) | 109.5(7) | H(48A)—C(48)—H(48C) | 109.5(6) |
| H(48B)—C(48)—H(48C) | 109.5(6) | C(42)—C(49)—H(49A) | 109.5(6) |
| C(42)—C(49)—H(49B) | 109.5(6) | C(42)—C(49)—H(49C) | 109.5(6) |
| H(49A)—C(49)—H(49B) | 109.5(7) | H(49A)—C(49)—H(49C) | 109.5(7) |
| H(49B)—C(49)—H(49C) | 109.5(7) | C(33)—C(50)—H(50A) | 109.5(6) |
| C(33)—C(50)—H(50B) | 109.5(6) | C(33)—C(50)—H(50C) | 109.5(7) |
| H(50A)—C(50)—H(50B) | 109.5(8) | H(50A)—C(50)—H(50C) | 109.5(7) |
| H(50B)—C(50)—H(50C) | 109.5(7) | C(42)—C(51)—H(51A) | 109.5(6) |
| C(42)—C(51)—H(51B) | 109.5(6) | C(42)—C(51)—H(51C) | 109.5(6) |
| H(51A)—C(51)—H(51B) | 109.5(7) | H(51A)—C(51)—H(51C) | 109.5(7) |
| H(51B)—C(51)—H(51C) | 109.5(7) | | |

TABLE 5

Complete listing of torsion angles

| Atoms | Angle |
|---|---|
| C(15)—O(4)—C(30)—O(1) | 172.5 |
| C(30)—O(4)—C(15)—C(12) | −158.2 |
| C(15)—O(4)—C(30)—O(8) | −8.1 |
| C(30)—O(4)—C(15)—C(22) | 19.9 |
| C(14)—N(5)—C(36)—O(7) | 164.3 |
| C(14)—N(5)—C(36)—O(5) | −14.9 |
| C(36)—N(5)—C(14)—C(23) | −160.3 |
| C(36)—N(5)—C(14)—C(32) | 20.9 |
| O(2)—C(8)—C(12)—C(15) | −23.2 |
| O(2)—C(8)—C(12)—C(16) | 158.5 |
| N(11)—O(9)—N(10)—O(21) | 162.8 |
| N(11)—O(9)—N(10)—O(24) | −37.7 |
| N(10)—C(9)—C(26)—O(19) | −172.2 |
| C(26)—C(9)—N(10)—C(21) | −6.1 |
| C(26)—C(9)—N(10)—C(24) | 153.4 |
| N(10)—C(9)—C(26)—C(29) | 8.0 |
| N(11)—C(9)—C(26)—O(19) | 18.5 |
| N(11)—C(9)—C(26)—C(29) | −161.3 |
| C(9)—N(10)—C(21)—C(29) | 1.9 |
| C(9)—N(10)—C(21)—C(35) | −177.4 |
| C(9)—N(10)—C(24)—O(3) | 4.7 |
| C(9)—N(10)—C(24)—O(9) | −175.5 |
| C(21)—N(10)—C(24)—O(3) | 160.5 |
| C(21)—N(10)—C(24)—O(9) | −19.6 |
| C(24)—N(10)—C(21)—C(29) | −156.6 |
| C(24)—N(10)—C(21)—C(35) | 24.1 |
| C(8)—C(12)—C(15)—O(4) | 0.9 |
| C(8)—C(12)—C(15)—C(22) | −177.2 |
| C(8)—C(12)—C(16)—H(16) | −2.7 |
| C(8)—C(12)—C(16)—C(28) | 177.2 |
| C(16)—C(12)—C(15)—O(4) | 179.2 |
| C(15)—C(12)—C(16)—H(16) | 178.9 |
| C(16)—C(12)—C(15)—C(22) | 1.1 |
| C(15)—C(12)—C(16)—C(28) | −1.1 |
| N(5)—C(14)—C(23)—C(25) | −2.1 |
| N(5)—C(14)—C(23)—C(31) | 177.8 |
| N(5)—C(14)—C(32)—H(32) | 0.9 |
| N(5)—C(14)—C(32)—C(38) | −179.2 |
| C(32)—C(14)—C(23)—C(25) | 176.8 |
| C(32)—C(14)—C(23)—C(31) | −3.3 |
| C(23)—C(14)—C(32)—H(32) | −177.8 |
| C(23)—C(14)—C(32)—C(38) | 2.2 |
| O(4)—C(15)—C(22)—H(22) | 2.0 |
| O(4)—C(15)—C(22)—C(34) | −178.0 |
| C(12)—C(15)—C(22)—H(22) | −179.9 |
| C(12)—C(15)—C(22)—C(34) | 0.1 |
| C(12)—C(16)—C(28)—H(28) | 180.0 |
| C(12)—C(16)—C(28)—C(34) | 0.0 |
| H(16)—C(16)—C(28)—H(28) | 0.0 |
| H(16)—C(16)—C(28)—C(34) | 180.0 |
| N(10)—C(21)—C(29)—C(26) | 3.4 |
| N(10)—C(21)—C(29)—C(43) | −179.1 |
| N(10)—C(21)—C(35)—H(35) | −0.3 |
| N(10)—C(21)—C(35)—C(41) | 179.7 |
| C(35)—C(21)—C(29)—C(26) | −177.2 |
| C(29)—C(21)—C(35)—H(35) | −179.5 |
| C(29)—C(21)—C(35)—C(41) | 0.5 |
| C(35)—C(21)—C(29)—C(43) | 0.3 |
| C(15)—C(22)—C(34)—C(28) | −1.3 |
| C(15)—C(22)—C(34)—H(34) | 178.8 |
| H(22)—C(22)—C(34)—C(28) | 178.7 |
| H(22)—C(22)—C(34)—H(34) | −1.3 |
| C(14)—C(23)—C(25)—O(6) | −177.3 |
| C(14)—C(23)—C(31)—H(31) | −177.1 |
| C(14)—C(23)—C(31)—C(44) | 2.9 |
| C(31)—C(23)—C(25)—O(6) | 2.8 |
| C(25)—C(23)—C(31)—H(31) | 2.7 |
| C(25)—C(23)—C(31)—C(44) | −177.3 |
| C(9)—C(26)—C(29)—C(21) | −7.0 |
| C(9)—C(26)—C(29)—C(43) | 175.7 |
| O(19)—C(26)—C(29)—C(21) | 173.2 |
| O(19)—C(26)—C(29)—C(43) | −4.1 |
| O(39)—O(27)—O(37)—H(37A) | 53.2 |
| O(39)—O(27)—O(37)—H(37B) | −66.8 |
| O(39)—O(27)—O(37)—H(37C) | 173.2 |
| O(37)—O(27)—O(39)—H(39A) | −177.2 |
| O(37)—O(27)—O(39)—H(39B) | 62.8 |
| O(37)—O(27)—O(39)—H(39C) | −57.2 |

TABLE 5-continued

Complete listing of torsion angles

| | |
|---|---|
| O(46)—O(27)—O(37)—H(37A) | 178.6 |
| O(46)—O(27)—O(37)—H(37B) | 58.6 |
| O(46)—O(27)—O(37)—H(37C) | −61.4 |
| O(37)—O(27)—O(46)—H(46A) | 56.1 |
| O(37)—O(27)—O(46)—H(46B) | −63.9 |
| O(37)—O(27)—O(46)—H(46C) | 176.1 |
| O(46)—O(27)—O(39)—H(39A) | 57.1 |
| O(46)—O(27)—O(39)—H(39B) | −62.9 |
| O(46)—O(27)—O(39)—H(39C) | 177.1 |
| O(39)—O(27)—O(46)—H(46A) | −179.8 |
| O(39)—O(27)—O(46)—H(46B) | 60.2 |
| C(39)—C(27)—C(46)—H(46C) | −59.8 |
| C(16)—C(28)—C(34)—C(22) | 1.2 |
| C(16)—C(28)—C(34)—H(34) | −178.8 |
| H(28)—C(28)—C(34)—C(22) | −178.8 |
| H(28)—C(28)—C(34)—H(34) | 1.2 |
| C(21)—C(29)—C(43)—C(40) | −1.0 |
| C(21)—C(29)—C(43)—H(43) | 179.0 |
| C(26)—C(29)—C(43)—C(40) | 176.0 |
| C(26)—C(29)—C(43)—H(43) | −4.0 |
| C(23)—C(31)—C(44)—C(38) | −1.4 |
| C(23)—C(31)—C(44)—H(44) | 178.6 |
| H(31)—C(31)—C(44)—C(38) | 178.6 |
| H(31)—C(31)—C(44)—H(44) | −1.4 |
| C(14)—C(32)—C(38)—H(38) | 179.3 |
| C(14)—C(32)—C(38)—C(44) | −0.7 |
| H(32)—C(32)—C(38)—H(38) | −0.7 |
| H(32)—C(32)—C(38)—C(44) | 179.3 |
| O(48)—O(33)—O(47)—H(47A) | −176.1 |
| O(48)—O(33)—O(47)—H(47B) | 63.9 |
| O(48)—O(33)—O(47)—H(47C) | −56.1 |
| O(47)—O(33)—O(48)—H(48A) | 60.3 |
| O(47)—O(33)—O(48)—H(48B) | −59.7 |
| O(47)—O(33)—O(48)—H(48C) | −179.7 |
| O(50)—O(33)—O(47)—H(47A) | 59.0 |
| C(50)—C(33)—C(47)—H(47B) | −61.0 |
| C(50)—C(33)—C(47)—H(47C) | 179.0 |
| C(47)—C(33)—C(50)—H(50A) | 179.4 |
| C(47)—C(33)—C(50)—H(50B) | 59.4 |
| C(47)—C(33)—C(50)—H(50C) | −60.6 |
| C(50)—C(33)—C(48)—H(48A) | −173.6 |
| C(50)—C(33)—C(48)—H(48B) | 66.4 |
| C(50)—C(33)—C(48)—H(48C) | −53.5 |
| C(48)—C(33)—C(50)—H(50A) | 54.6 |
| C(48)—C(33)—C(50)—H(50B) | −65.4 |
| C(48)—C(33)—C(50)—H(50C) | 174.6 |
| C(21)—C(35)—C(41)—C(40) | −0.4 |
| C(21)—C(35)—C(41)—H(41) | 179.6 |
| H(35)—C(35)—C(41)—C(40) | 179.6 |
| H(35)—C(35)—C(41)—H(41) | −0.4 |
| C(32)—C(38)—C(44)—C(31) | 0.4 |
| C(32)—C(38)—C(44)—H(44) | −179.6 |
| H(38)—C(38)—C(44)—C(31) | −179.6 |
| H(38)—C(38)—C(44)—H(44) | 0.4 |
| H(40)—C(40)—C(41)—C(35) | 179.6 |
| H(40)—C(40)—C(41)—H(41) | −0.4 |
| H(40)—C(40)—C(43)—C(29) | −178.9 |
| H(40)—C(40)—C(43)—H(43) | 1.1 |
| C(41)—C(40)—C(43)—C(29) | 1.1 |
| C(43)—C(40)—C(41)—C(35) | −0.4 |
| C(43)—C(40)—C(41)—H(41) | 179.6 |
| C(41)—C(40)—C(43)—H(43) | −178.9 |
| C(49)—C(42)—C(45)—H(45A) | 170.1 |
| C(49)—C(42)—C(45)—H(45B) | 50.1 |
| C(49)—C(42)—C(45)—H(45C) | −69.9 |
| C(45)—C(42)—C(49)—H(49A) | −179.6 |
| C(45)—C(42)—C(49)—H(49B) | 60.4 |
| C(45)—C(42)—C(49)—H(49C) | −59.6 |
| C(51)—C(42)—C(45)—H(45A) | 43.8 |
| C(51)—C(42)—C(45)—H(45B) | −76.2 |
| C(51)—C(42)—C(45)—H(45C) | 163.8 |
| C(45)—C(42)—C(51)—H(51A) | 179.6 |
| C(45)—C(42)—C(51)—H(51B) | 59.6 |
| C(45)—C(42)—C(51)—H(51C) | −60.4 |
| C(51)—C(42)—C(49)—H(49A) | −52.2 |

TABLE 5-continued

Complete listing of torsion angles

| | |
|---|---|
| C(51)—C(42)—C(49)—H(49B) | −172.2 |
| C(51)—C(42)—C(49)—H(49C) | 67.8 |
| C(49)—C(42)—C(51)—H(51A) | 52.6 |
| C(49)—C(42)—C(51)—H(51B) | −67.4 |
| C(49)—C(42)—C(51)—H(51C) | 172.6 |

Example 2

UV Absorption of Solutions Containing a Representative Compound of the Invention at Different pHs 1 mg of pH sensitive compound of Example 1 of EP application No. 19190058 is weighed and dissolved in 10 ml of a solvent mixture made of DMSO:$H_2O$ [9:1]. The concentration of the resulting solution is $1.43 \times 10^{-4}$ M.

To modify the pH of the solutions to be tested, NaOH was used instead of water in the above mixture (see Table 1).

The pH values of the solutions were measured after adding 1 mL of NaOH solution at different concentration to the pH-sensitive compound dissolved in 9 ml of DMSO, by a pH-meter.

TABLE 1

NaOH concentrations and corresponding pH values of the resulting solutions

| No | NaOH concentration | pH |
|---|---|---|
| 1 | 0M | 6.0 |
| 2 | 0.00025M | 6.8 |
| 3 | 0.0005M | 7.4 |
| 4 | 0.00075M | 7.7 |
| 5 | 0.001M | 8.0 |
| 6 | 0.0015M | 8.8 |
| 7 | 0.0020M | 10.4 |
| 8 | 0.0025M | 11.3 |

The prepared solutions were tested by a UV-Vis Beckman Coulter DU 800 spectrophotometer.

As it can be seen in FIG. 5, the corresponding wavelength of the maximum absorption of pH-sensitive compound at pH 6 is 486 nm. The corresponding wavelength of the maximum absorption of the compound changes from 486 nm to 593 nm (yellow to blue) depending on increasing pH.

Not only the wavelength of the maximum absorption but also the intensity of the absorbance changes, due to the altering of the chemical structure of the pH-sensitive compound into the solution (see FIG. 5).

These wavelength shifts are also visually observed on the solutions and textiles dyed with the pH-sensitive compound, which turns from yellow to blue upon increasing the pH of different washing solutions.

The invention claimed is:
1. A compound of formula (I)

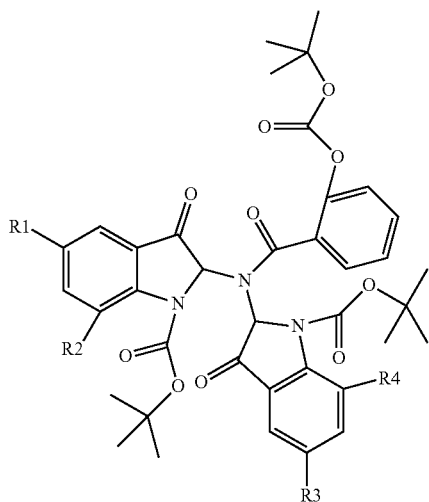

(I)

wherein R$_1$, R$_2$, R$_3$ and R$_4$ are, each independently, selected from a hydrogen atom, an alkyl group, an alkoxy group, a hydroxy group and a halogen atom, and salts and/or solvates thereof.

2. The compound according to claim 1, wherein R$_1$, R$_2$, R$_3$ and R$_4$ are all a hydrogen atom.

3. A process for the preparation of a compound of formula (I) or a salt and/or solvate thereof, which comprises reacting a t-Boc-protected indigo of formula (II)

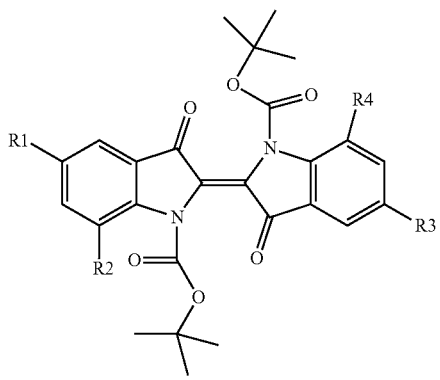

(II)

wherein R$_1$, R$_2$, R$_3$ and R$_4$ are as defined in claim 1, with sodium amide in an organic solvent, adding an acid to obtain an acidic pH, isolating the compounds of formula (I) and, optionally, converting it into one of its salts.

4. The process of claim 3, wherein said solvent is an alcohol.

5. A compound selected from compounds (IIIA) and (IIIB)

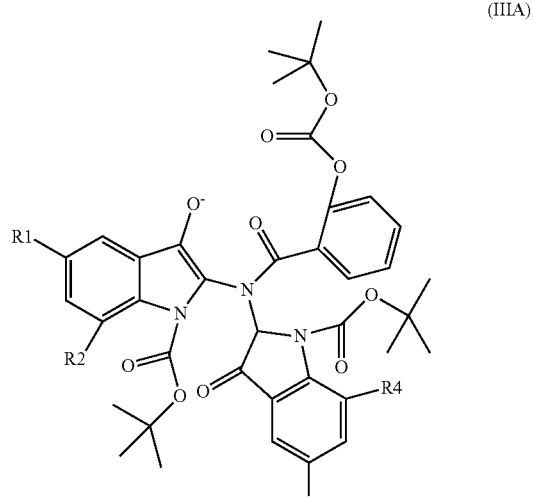

(IIIA)

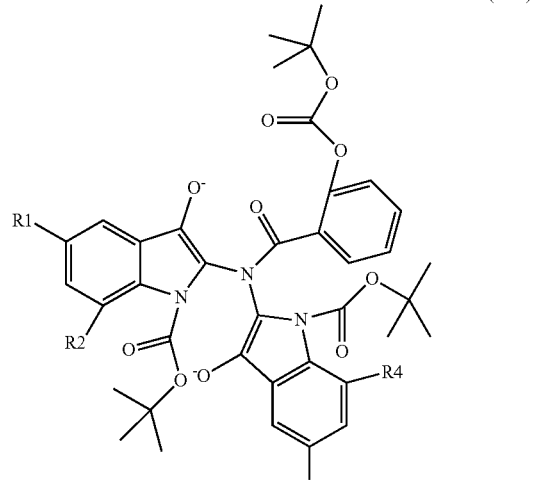

(IIIB)

in the presence of a counter-ion, wherein R$_1$, R$_2$, R$_3$ and R$_4$ are defined as in claim 1.

6. A method for dyeing textile materials which comprises applying one or more compounds of formula (I) according to claim 1, onto a textile material.

7. The method of claim 6, wherein said one or more compounds of formula (I) are solubilized in an aqueous solvent or solvent mixture.

8. The method of claim 7, wherein the aqueous solvent or the solvent mixture is a water/alcohol mixture.

* * * * *